US00PP31780P2

(12) United States Plant Patent
Hansen

(10) Patent No.: US PP31,780 P2
(45) Date of Patent: May 19, 2020

(54) ***GERANIUM* PLANT NAMED 'CRANE DANCE'**

(50) Latin Name: ***Geranium maculatum* L.**
Varietal Denomination: Crane Dance

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,918

(22) Filed: Feb. 1, 2019

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./324
CPC ..... A01H 5/02; A01H 5/0277; A01H 5/00; A01H 6/42; A01H 6/425
See application file for complete search history.

(56) References Cited

U.S. PATENT DOCUMENTS

PP22,455 P2 * 1/2012 Delabroye ..... A01H 6/42 Plt./324
PP22,456 P2 * 1/2012 Klinkhamer ..... A01H 5/02 Plt./324

* cited by examiner

*Primary Examiner* — June Hwu

(57) ABSTRACT

The new and distinct hybrid of Hardy *Geranium* plant named 'Crane Dance' with palmately-lobed, deeply cleft foliage having deep green color with purple overlay and developing to brilliant reddish in the fall. The plant has numerous, densely-branched, stiff, erect, umbels with bluish-purple flowers displayed for two to three weeks beginning early summer. The new plant is vigorous and produces large upright mounded clumps suitable for landscape use in full-sun to medium-shaded garden.

2 Drawing Sheets

Botanical denomination: *Geranium maculatum* L.
Variety denomination: 'Crane Dance'.

STATEMENT REGARDING PRIOR DISCLOSURES UNDER 37 CFR 1.77(b)(6)

The first public disclosure of the claimed plant, in the form of a photograph and brief description on a website operated by Walters Gardens, Inc. on Feb. 1, 2018. The claimed plant was first sold on Jan. 7, 2019 by Walters Gardens, Inc., who obtained the plant and all information relating thereto, from the inventor. No plants of *Geranium* 'Crane Dance' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Hardy *Geranium* in the Geraniaceae family and given the cultivar name of 'Crane Dance'. *Geranium* 'Crane Dance' was hybridized by the inventor on May 17, 2012 at a wholesale perennial nursery in Zeeland, Mich., USA. The seed or female parent was *Geranium maculatum* 'Espresso' (not patented) and the pollen or male parent was *Geranium maculatum* 'Elizabeth Ann' U.S. Plant Pat. No. 11,252. Seeds resulting from this cross were harvested in the summer of 2012 and sown later in fall of 2012 at the same nursery.

*Geranium* 'Crane Dance' was first selected in the summer of 2014 and assigned the breeder code 12-43-3 through the final evaluation process in the fall of 2016. *Geranium* 'Crane Dance' has been asexually propagated by separation of the rhizomes at the same nursery in Zeeland, Mich. in 2016 and the resultant plants have remained stable and continued to exhibit the same characteristics as the original plant for multiple generations.

BRIEF SUMMARY OF THE INVENTION

The nearest comparison varieties known to the inventor are the parents: 'Espresso' and 'Elizabeth Ann'. 'Espresso' is shorter and has darker foliage with rounder leaf apices, and it is less floriferous than the new plant. 'Elizabeth Ann' is smaller in habit, has darker foliage and has a flower more on the violet color spectrum. 'Midnight Clouds' U.S. Plant Pat. No. 22,456 has flowers that are very pale purple, a lighter coloration with a hue closer to pink, rather than the very light purple of the new plant with a hue closer to violet. 'Midnight Clouds' is also not known to develop foliage with bright reddish coloration in the fall. 'Midnight Blues' U.S. Plant Pat. No. 22,455 has shorter habit, smaller flowers, the petals are not as violet on the back and fade to a very pale purple.

*Geranium* 'Crane Dance' differs from its parents as well as all other Hardy *Geranium* known to the applicant in the following combined traits:

1. The foliage is round, dark-green with an overlay of purple, deeply-cleft, palmately-lobed;
2. Flowers with bluish-purple petals on heavily branched umbels;

3. Foliage develops a bright reddish coloration in fall.
4. Growth is vigorous and refined.

BRIEF DESCRIPTION OF THE DRAWINGS

The photographs of the new plant demonstrate the overall appearance of the plant including the unique traits. The plants in the drawing are of plants growing in a full-sun research garden in Zeeland, Mich. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
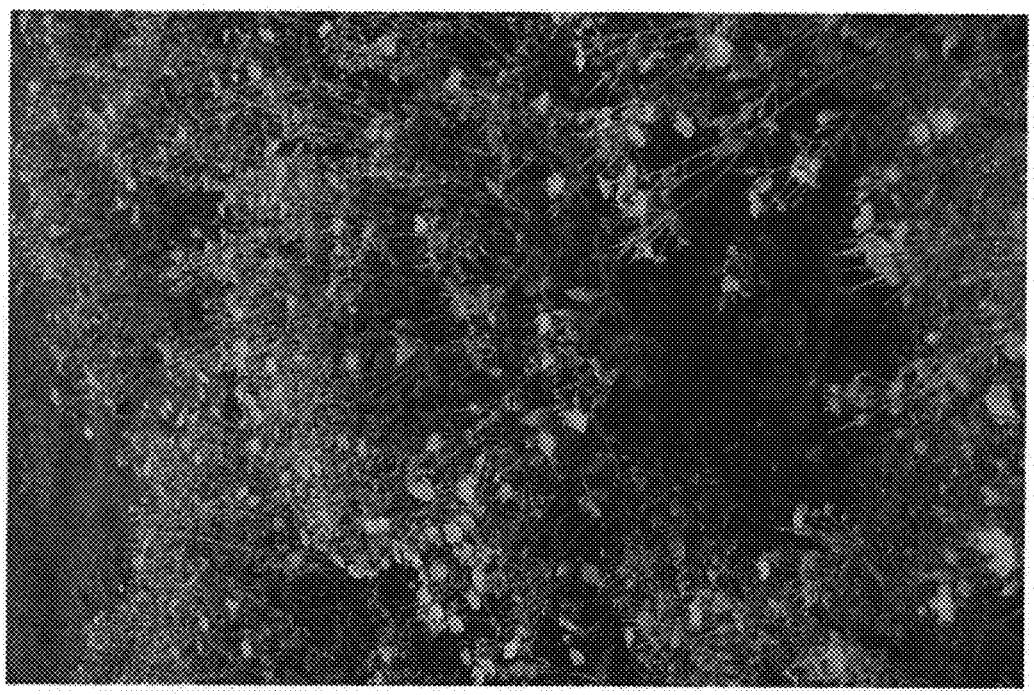
FIG. 1 shows a four-year-old plant in the landscape in peak flower.
Figure 2:
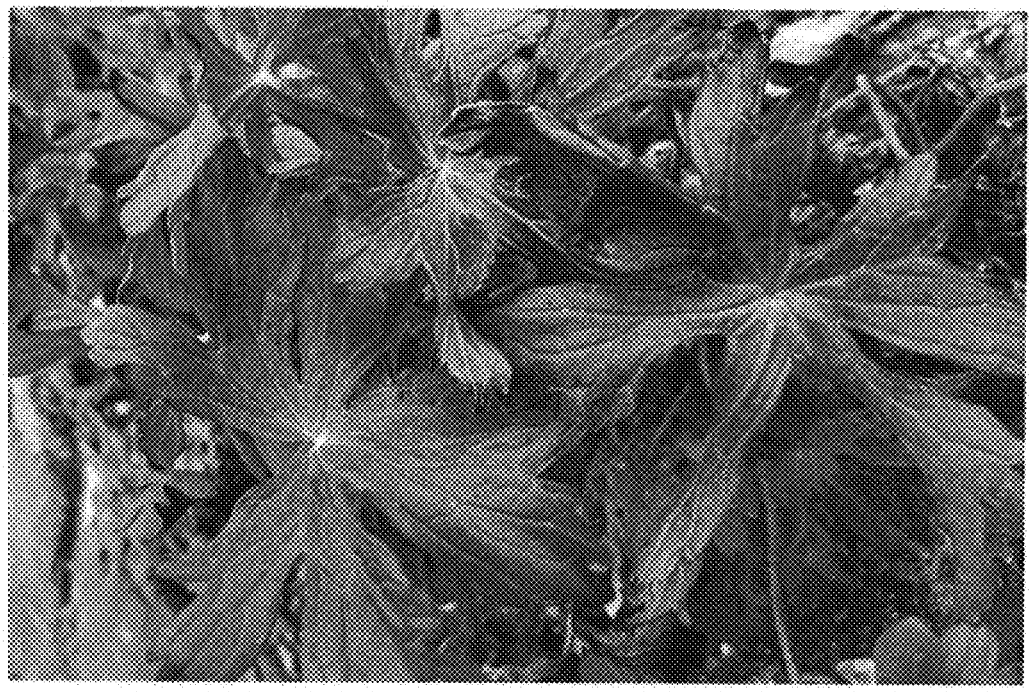
FIG. 2 shows a close-up of the reddish fall coloration on a one-year-old plant.
Figure 3:
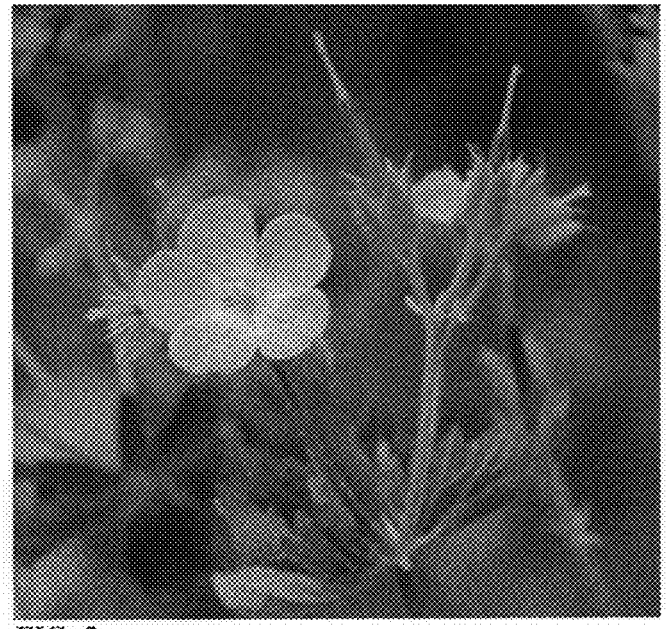
FIG. 3 shows a close-up of the flower and young fruit of a four-year-old plant.

The following description is based on a four-year-old plant growing in a full-sun trial garden in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 'Espresso', the male or pollen parent was 'Elizabeth Ann';

Plant habit: Winter-hardy herbaceous perennial with multiple upright stems; 70.0 cm tall and 75.0 cm in diameter; with about 10 upright branched stems per plant;

Roots: Fibrous; thick; finely branched;

Growth rate: Rapid, finishing a 3.8 liter contain in eight to ten weeks;

Foliage: Opposite; palmately-rounded; deeply-cleft to near petiole, typically penta-lobed with each lobe frequently dissected in distal one-third, with four main deep incisions and two to four irregularly moderate to shallow lobe incisions; lobe apices acute; base semi-peltate to hastate; margins micro-serrate; adaxial and abaxial matte; puberulent to minutely puberulent adaxial and abaxial; rugosity absent to very weak;

Leaf blade size: To about 12.0 cm wide and 10.5 cm long;

Leaf color: Mature adaxial between RHS NN137A and RHS 137A with slight undertone nearest RHS N186B in high ultraviolet light intensity, base of lobes between RHS 145A and RHS 146D; mature abaxial between RHS 148D and RHS 191D; fall adaxial variable with combinations of nearest RHS 187B and RHS 53B, fall abaxial nearest RHS 53D; young adaxial nearest RHS 138B, young abaxial nearest RHS 138D;

Leaf quantity: Dense, about 200 per plant;

Veins: Palmate, puberulent abaxial and glabrous adaxial;

Vein color: Adaxial main veins nearest RHS 148D and secondary and distal veins same as surrounding leaf; abaxial main veins between RHS 148D and RHS 191D; fall adaxial and abaxial nearest RHS 53D;

Petiole: Cylindrical; pubescent; to about 7.5 cm long and 2.5 mm diameter at base;

Petiole color: Nearest RHS 138B;

Stipule: Two per node; lanceolate; narrowly apex acute, base truncate, clasping; to about 10.0 mm long and 3.5 mm wide at base;

Stipule color: Nearest RHS 161C;

Peduncle: Umbel; cylindrical; wiry, stiff; puberulent; upright; branched; to about 25.0 cm long and 3.5 mm diameter at base, average about 22.0 cm tall and 3.2 mm diameter; flowering in upper 18 cm with about 50 flowers per umbel;

Flowering longevity: Inflorescence effective for about two to three weeks; individual flowers about 5 to 7 days; petals self-cleaning;

Peduncle color: Nearest RHS 146C with blushing of nearest RHS 183A in portions getting high ultraviolet light;

Pedicel: Cylindrical, puberulent; to about 10.0 mm long and 1.0 mm diameter, average about 6.0 mm long and 0.7 mm diameter; attitude upright to outwardly;

Pedicel color: Nearest RHS 185B;

Nodes: About 6 per stem; swollen to about 5.0 mm diameter; color nearest RHS 145D;

Internode length: About 8.0 cm;

Buds one day prior to opening: Ellipsoidal; acute apex and rounded base; about 12.0 mm long and 6.0 mm diameter near middle;

Bud color one day prior to opening: Calyx nearest RHS 138B with exposed petals nearest RHS 85C;

Inflorescence size: Average about 11.5 cm across and 8 cm tall;

Flower: Perfect; campanulate; actinomorphic; about 35.0 mm wide and 12.0 mm deep; nearly flat when fully mature;

Flower attitude: Upwardly to slightly outwardly;

Petals: Five; broadly obovate; rounded apex and attenuate base; entire margin; glabrous abaxial and adaxial; about 18.0 mm long and 12.0 mm wide in middle; weakly overlapping; petal veins very weak;

Petal color: Adaxial nearest RHS 85C with center eye nearest RHS NN155D and veins in proximal one-half of petals nearest RHS 94A; abaxial nearest RHS 94D;

Calyx: Rotate; about 7.5 mm deep and 23.0 mm wide at apex;

Sepals: Five; ovate; mucronate apex; pubescent abaxial; matte, glabrous adaxial; base truncate; to about 15.0 mm long and 5.0 mm wide near middle;

Sepal color: Abaxial apex nearest RHS 138B, nearest RHS 145A adaxial;

Androecium: Ten;

*Filaments*.—Ten, thin, glabrous; about 4.5 mm long and less than 0.3 mm diameter; color nearest RHS 155D.

*Anthers*.—Ellipsoidal, dorsifixed, longitudinal; about 2.0 mm long and about 0.5 mm across; color nearest RHS 92A.

*Pollen*.—Abundant; color nearest RHS 18D.

Gynoecium: Single; about 12.0 mm long;

*Style*.—About 6.0 mm long and about 0.7 mm diameter; color nearest RHS 161C.

*Stigma*.—Penta-fid; about 3.0 mm long and 0.3 mm diameter; color nearest RHS 158B.

*Ovary*.—Ellipsoidal; about 3.0 mm long and 1.5 mm diameter; color nearest RHS 200A.

Fruit: Beak-like, oblong capsule with five spring arms with persistent style; before dehiscing about 40.0 mm long and 4.0 mm diameter in middle; color upon ripening nearest RHS 177A;

Seeds: Nutlet; about 2.0 mm across and 2.0 mm long; color nearest 200A;

Disease and pest tolerance: The new plant grows best with ample moisture and drainage in either part sun or full shade. Cold hardy from USDA zones 4 to 8. Other resistance and tolerance outside of that normal for Hardy *Geranium* is not known.

It is claimed:

1. The new and distinct Hardy *Geranium* plant named *Geranium* 'Crane Dance' as herein described and illustrated.

* * * * *